United States Patent [19]

Raftopoulos et al.

[11] 4,453,539

[45] Jun. 12, 1984

[54] EXPANDABLE INTRAMEDULLARY NAIL FOR THE FIXATION OF BONE FRACTURES

[75] Inventors: Demetrios D. Raftopoulos; James D. Baril; Glenn Reimer, all of Toledo, Ohio

[73] Assignee: The University of Toledo, Toledo, Ohio

[21] Appl. No.: 353,511

[22] Filed: Mar. 1, 1982

[51] Int. Cl.³ .............................................. A61F 5/04
[52] U.S. Cl. ............................................... 128/92 BC
[58] Field of Search ............ 128/92 BC, 92 B, 92 BA

[56] References Cited

U.S. PATENT DOCUMENTS 3,986,504 10/1976 Avila ............................... 128/92 BC
4,204,531 5/1980 Aginsky .......................... 128/92 BC

FOREIGN PATENT DOCUMENTS 453570 6/1968 Switzerland ................... 128/92 BC

*Primary Examiner*—John D. Yasko
*Attorney, Agent, or Firm*—Fraser, Barker, Purdue & Clemens

[57] ABSTRACT

The present invention relates to an improved expandable intramedullary nail for the fixation of bone fractures. The nail includes an elongate sleeve having one end adapted to be inserted within the medullary cavity of the bone. The one end of the sleeve is formed of a predetermined maximum retracted diameter to permit the insertion of the one end within the bone cavity. A plurality of circumferentially spaced, radially expandable elements are carried by the one end of the sleeve. The elements are radially movable from a first, retracted position wherein the elements define a first diameter to a second, expanded position wherein the elements define a second diameter greater than the predetermined maximum retracted diameter and the first diameter. In accordance with the present invention, when the elements are in the expanded position, the elements provide at least two support points at the second diameter and axially spaced along the sleeve for engagement with the inner wall of the bone cavity. A camming member is carried by the one end of the elongate sleeve for moving the elements from the retracted position to the expanded position. An actuator is located at the other end of the sleeve and is coupled to operate the camming member for controlling the radial position of the elements.

6 Claims, 10 Drawing Figures

EXPANDABLE INTRAMEDULLARY NAIL FOR THE FIXATION OF BONE FRACTURES

BACKGROUND OF THE INVENTION

The present invention relates generally to intramedullary nails for the fixation of bone fractures and, in particular, to intramedullary nails having an expandable portion for securely maintaining the nail within the medullary cavity of one of the fractured bone portions.

The use of intramedullary nailing for the fixation of bone fractures is well known. Such a procedure rejoins and reinforces the broken bone portions of a body limb and, in many instances, permits the functional rehabilitation of the limb within a relatively short time.

The earliest types of intramedullary nails consisted of a single diameter rod constructed of a non-corrosive material. Typically, the diameter of the nail was selected to correspond with the narrowest part of the medullary cavity of the bone into which the nail was to be inserted. Since the diameter of these nails was relatively thin throughout the length of the bone, the nails were usually not strong enough to take up the stresses originally carried by the bone. This problem was especially evident in larger bones such as, for example, the femur. Consequently, in these instances, the limb had to be immobilized for a relatively long period, which not only rendered the patient unfit for work during that time but also involved the danger of muscle atrophy and other ailments associated with prolonged convalescence.

In order to hasten the return of mobility of the damaged limb, it became necessary to use stronger nails. The use of a larger diameter nail was made possible by enlarging the medullary cavity by reaming the bone. Typically, such a nail was constructed with a uniform cross section throughout its entire length except for the front tip which was tapered inwardly to assist in the insertion of the nail through the bone marrow. However, the principal drawback of this type of nail is that the practice of enlarging the medullary cavity tends to weaken the shaft of the bone and reduce the blood supply to the fractured ends, thereby impeding the healing process.

Another problem associated with the above-described intramedullary nails is that, in some instances, the lateral support provided by the nail is very limited due to the construction of tubular bones. Typically, tubular bones have a longitudinally extending, marrow-containing cavity having a contour which converges in the central portion of the bone and then diverges in a longitudinal direction near the ends of the bone. Consequently, an intramedullary nail having a uniform cross section will typically only contact the inner wall of the medullary cavity of the bone only over a small region. Such a nail provides only limited lateral support between the fractured bone portions.

One approach to providing increased lateral support at the fracture was to use an intramedullary nail having an expandable end portion. Such a nail has a retracted diameter in the end portion which permits the nail to be inserted through the convergent portion of the medullary cavity, and thereafter expanded to engage the increased diameter inner wall of the divergent portion. Such expansion nails have resulted in increased lateral retention of the fractured bone portions but are relatively expensive and sometimes require complex devices to effect the expansion of the end portion. Typical examples of such prior art expandable nails are shown in U.S. Pat. Nos. 3,760,802, 3,530,854 and 4,091,806.

SUMMARY OF THE INVENTION

The present invention relates to an improved intramedullary nail for the fixation of bone fractures. One improved feature of the nail relates to a unique expanding portion which is designed to effectively engage the inner wall of the divergent portion of the medullary cavity of the bone.

Generally, the nail includes an elongate member having one end adapted to be inserted within the medullary cavity of the bone. The one end of the elongate member is formed of a predetermined maximum retracted diameter to permit the insertion of the one end within the bone cavity. A plurality of circumferentially spaced, radially expandable elements are carried by the one end of the elongate member. The elements are radially movable from a first, retracted position wherein the elements define a first diameter to a second, expanded position wherein the elements define a second diameter greater than the predetermined maximum retracted diameter and the first diameter. In accordance with the present invention, when the elements are in the expanded position, the elements provide at least two support points at the second diameter, with these points being axially spaced along the elongate member for engagement with the inner wall of the bone cavity. Means are carried by the elongate member for moving the elements from the retracted position to the expanded position and an actuator means is located at the other end of the elongate member and coupled to operate the moving means for controlling the radial position of the expanding elements.

The present invention includes at least two embodiments. In one embodiment, the radially expandable elements are each provided with an axially extending outer surface which, when the elements are in the expanded position, provides at least two axially spaced apart support points at a selected diameter for engagement with the inner wall of the bone cavity.

In an alternate embodiment of the invention, the radially expandable elements comprise generally spherical balls arranged in axially spaced apart groups, with each group including a plurality of circumferentially spaced apart balls. The radial position of the balls is controlled such that, when the balls are in the expanded position, a ball of one group cooperates with a ball of another group to provide two axially spaced apart support points at a selected diameter for engagement with the inner wall of the bone cavity.

DESCRIPTION OF THE PREFERRED EMBODIMENTS

Figure 1:
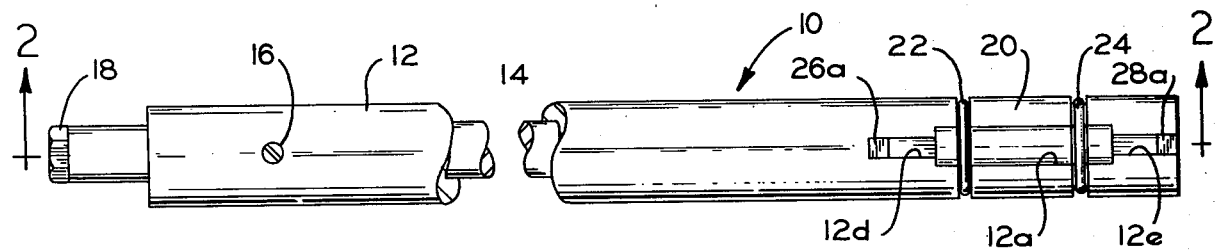
FIG. 1 is a elevational view of one embodiment of an expandable intramedullary nail embodying the principles of the present invention.

Referring to FIGS. 1 through 5, there is shown one embodiment of an expandable intramedullary nail 10 embodying the features of the present invention. Typically, the components of the nail 10 are constructed of a non-corrosive, biocompatible alloy such as, for example, stainless steel. The nail 10 includes an outer elongate sleeve 12 which houses an elongate actuating shaft 14 mounted for rotational movement within the sleeve 12. A set screw 16 is threaded into the side wall of the sleeve 12 and extends radially inwardly into an outer annular groove 14a formed in the actuating shaft 14. The set screw 16 permits rotative movement of the shaft 14 within the sleeve 12, but militates against any axial movement therebetween. The extreme one end of the shaft 14 extends axially past the one end of the sleeve 12 and is provided with a hexagonal head 18 for selective engagement with a suitable tool (not shown) for rotating the shaft 14.

Figure 2:
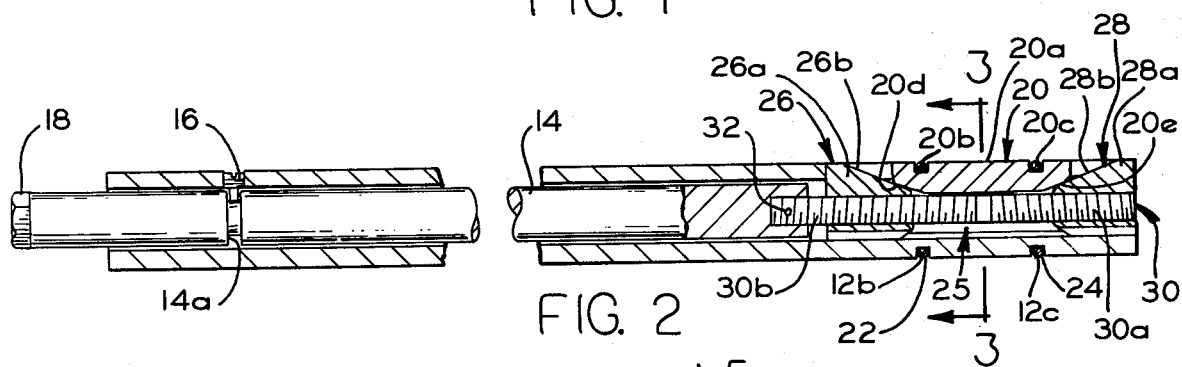
FIG. 2 is a longitudinal partially sectional view taken along the line 2—2 of FIG. 1.

The other end of the sleeve 12 is provided with a plurality of circumferentially spaced openings such as rectangular cutout portions 12a for receiving a plurality of generally rectangular, radially expandable segments 20. The segments 20 have an axially extending outer surface 20a which, as will be discussed, is expanded outwardly to engage the inner wall of a medullary cavity of a bone. As shown in FIG. 2, the segments 20 are each provided with spaced apart grooves 20b and 20c while the sleeve 12 is provided with corresponding spaced apart grooves 12b and 12c for receiving a pair of C-shaped spring clips 22 and 24, respectively. As will be discussed, the spring clips 22 and 24 bias the segments 20 radially inwardly into the openings 12a.

The radial position of the segments 20 is controlled by a cam means 25 coupled to the inner end of the actuating shaft 14. The cam means 25 includes a pair of axially spaced apart cooperating camming members 26 and 28 which are mounted on a threaded shaft 30. The outer end of the shaft 30 is provided with a right hand threaded portion 30a which threadably engages cooperating threads formed through the camming member 28. The inner end of the shaft 30 is provided with a left hand threaded portion 30b which threadably engages cooperating threads formed through the camming member 26. The inner end of the shaft 30 is threadably received within the inner end of the actuating shaft 14 and is secured thereto by means of a pin 32. The pin 32 prevents any relative rotative movement between the actuating shaft 14 and the threaded shaft 30.

The camming member 26 is provided with a plurality of circumferentially spaced fin elements 26a which extend radially outwardly into elongate slots 12d formed in the sleeve 12. Each fin element 26a includes an inclined surface 26b for engagement with an inner tapered surface 20d formed on one end of each of the segments 20. Similarly, the camming member 28 includes a plurality of circumferentially spaced fin elements 28a which extend outwardly into elongate slots 12e formed in the sleeve 12 and are provided with an inclined surface 28b for engagement with an inner tapered surface 20e formed on the other end of each of the segments 20.

The segments 20 can be moved radially outwardly by rotating the actuating shaft 14 and the threaded shaft 30 in one direction relative to the sleeve 12. As the actuating shaft 14 and the threaded shaft 30 are rotated in one direction, the right hand threads 30a and the left hand threads 30b on the shaft 30 will cooperate to cause the camming members 26 and 28 to move axially toward one another. As the members 26 and 28 are moved axially, the inclined surfaces 26b and 28b will engage the tapered surfaces 20d and 20e, respectively, to cause the segments 20 to move radially outwardly. As the segments 20 are moved outwardly, the C-shaped spring clips 22 and 24 will expand. Rotation of the actuating shaft 14 and the threaded shaft 30 in an opposite direction will move the camming members away from one another and thereby permit the spring clips 22 and 24 to return the segments to their retracted position.

Figures 3, 4:
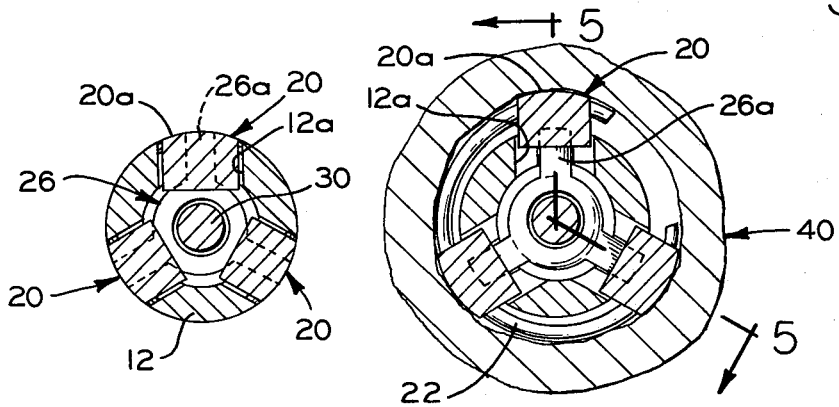
FIG. 3 is a cross-sectional view taken along line 3—3 of FIG. 2.
FIG. 4 is a sectional view, similar to FIG. 3, but showing the nail in an expanded position and located within the medullary cavity of a fractured bone.
Figure 5:
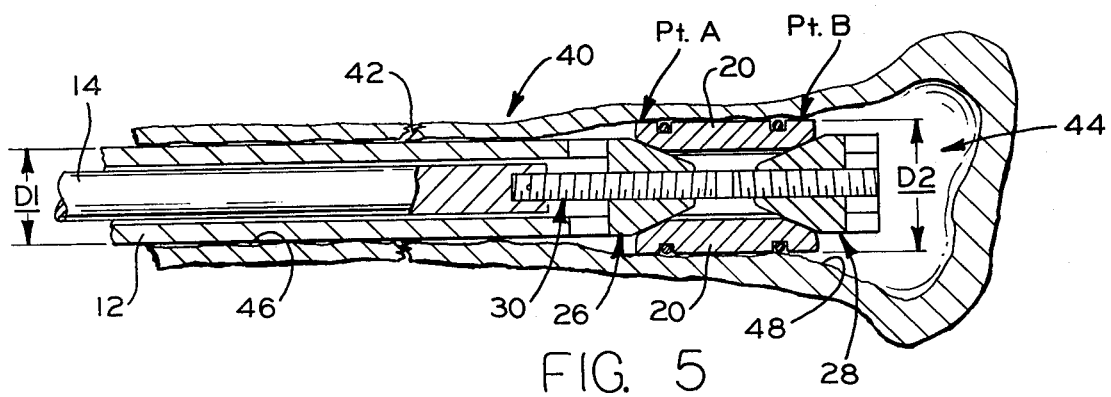
FIG. 5 is a sectional view taken along the line 5—5 of FIG. 4.
Figure 6:
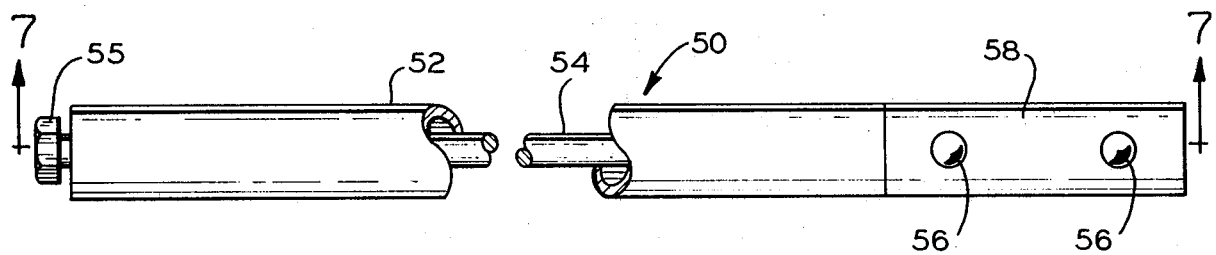
FIG. 6 is a side elevational view of an alternate embodiment of an expandable intramedullary nail according to the present invention.

FIGS. 4 and 5 illustrate the manner in which the nail 10 can be used to secure a fractured bone. In FIG. 4, a bone 40 having a fracture 42 is schematically shown in section. The bone includes an inner medullary canal 44 having a narrow convergent portion 46 and a larger diameter divergent portion 48. Typically, the nail 10 is selected to have a maximum retracted diameter D1 which corresponds to the diameter of the convergent portion 46. This permits the expandable end of the nail 10, when it is in a retracted position, to be inserted through the convergent portion 46 of the medullary cavity 44. Once the nail 10 has been inserted into the medullary cavity 44, the segments 20 can be expanded outwardly by rotating the actuating shaft 14 relative to the sleeve 12.

As shown in FIG. 4, the segments 20 are expanded to a diameter D2 such that the outer surfaces 20a of the segments 20 engage the inner wall of the divergent portion 48 of the medullary cavity 44. In accordance with the present invention, the expanded end of the nail 10 provides axially spaced apart support points (Pt. A and Pt. B) along the sleeve at the diameter D2. Such a support arrangement securely fixes the expandable end of the nail 10 within the divergent portion 48. After the bone fracture has healed, the segments 20 can be retracted to permit removal of the nail.

Referring to FIGS. 6 through 10, there is shown an alternate embodiment of an expandable intramedullary nail 50 embodying the principles of the present invention. The nail 50 includes an outer elongate sleeve 52 which houses an elongate actuating shaft 54. The actuating shaft 54 is provided with a threaded portion 54a which is threadably received within one end of the sleeve 52. The extreme end of the shaft 54 extends axially past the one end of the sleeve and is provided with a hexagonal head portion 55 for selective engagement with a suitable tool (not shown) for rotating the shaft 54.

The other end of the sleeve 52 has a reduced diameter portion 52a which is provided with a plurality of openings or apertures 52b for receiving a plurality of generally spherical, radially expandable balls 56. The balls 56 are arranged in separate, axially spaced apart groups, with each group including a plurality of circumferentially spaced balls. The apertures 52b are formed of a diameter slightly larger than the diameter of the balls 56. A retainer sleeve 58 is coaxially positioned over the reduced diameter portion 52a of the sleeve 52 and includes a plurality of apertures 58a which are aligned with the apertures 52b. The apertures 58a are formed of a diameter slightly less than the diameter of the balls 56 in order to maintain the balls 56 within the sleeve apertures 52b.

Figure 7:
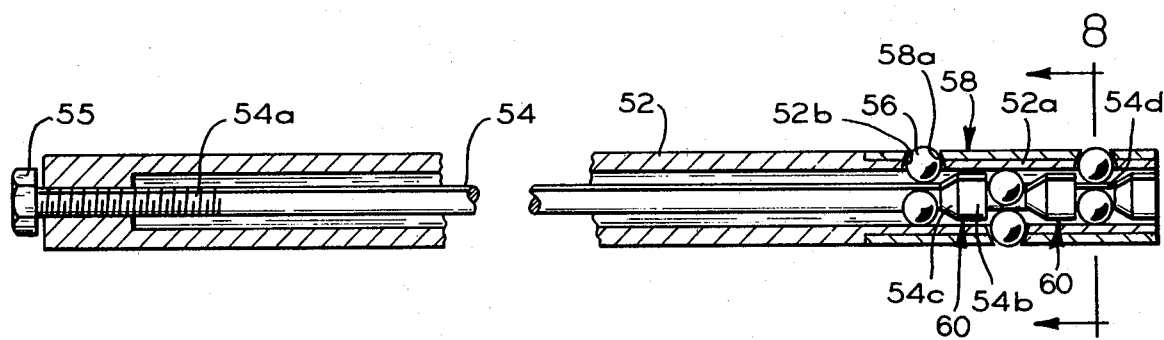
FIG. 7 is a longitudinal partial sectional view taken along the line 7—7 of FIG. 6.
Figure 8:
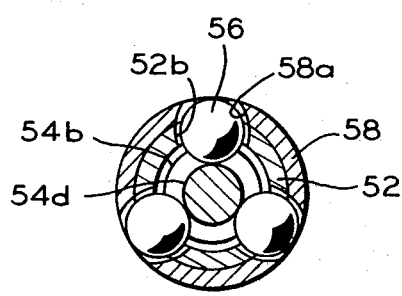
FIG. 8 is a sectional view taken along the line 8—8 of FIG. 7.

The actuating shaft 54 extends axially through the sleeve 52 and is provided with cam means 60 on one end thereof for controlling the radial position of the individual balls 56. As shown in FIG. 7, the cam means 60 includes a plurality of axially spaced apart, increased diameter portions 54b each of which taper radially inwardly to form a conical surface 54c which terminates at reduced diameter portions 54d. The conical surfaces 54c provide a means of adjusting the radial position of the balls 56 between a minimum retracted position wherein the balls engage the reduced diameter portion 54d to a maximum expanded position wherein the balls engage the increased diameter portions 54b.

The balls 56 can be moved radially outwardly by rotating the actuating shaft 54 in one direction relative to the sleeve 52. As the shaft 54 is rotated in one direction, the increased diameter portions 54b are moved axially toward the balls 56 until the conical surfaces 54c engage the balls 56. As the actuating shaft 54 is moved further axially, the conical surfaces 54c cause the balls 56 to move radially outwardly until they are resting upon the increased diameter portions 54b. Rotation of the actuating shaft 54 in an opposite direction will move the increased diameter portions out of engagement with the balls and permit the balls to return to a retracted position.

Figure 10:
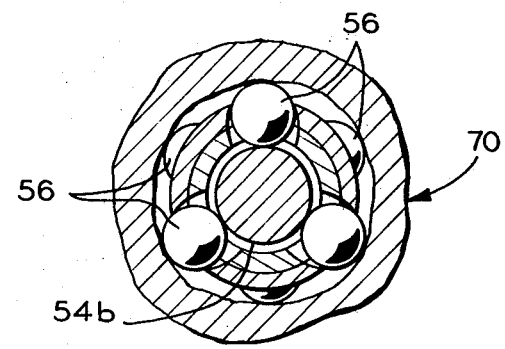
FIG. 10 is a sectional view taken along the line 10—10 of FIG. 9.
Figure 9:
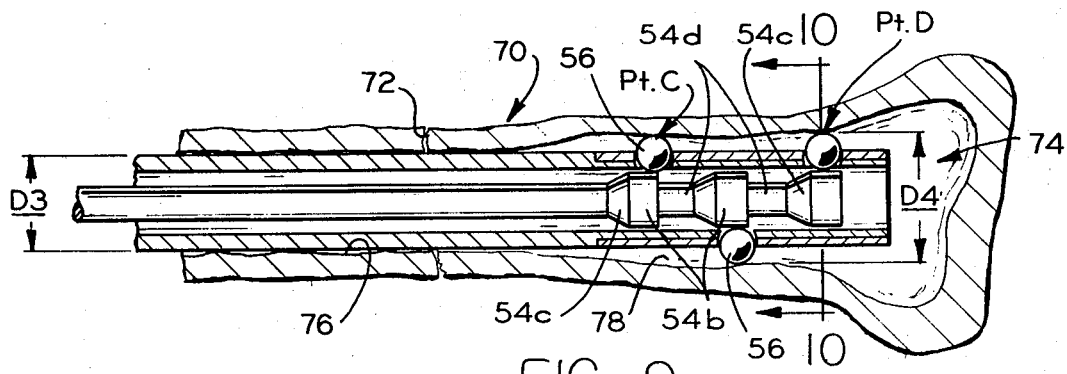
FIG. 9 is a sectional view, similar to FIG. 7, but showing the nail in an expanded position and located within a medullary cavity of a fractured bone.

Referring to FIGS. 9 and 10, there is shown the manner in which the nail 50 can be utilized to secure a fractured bone. In FIG. 9, a bone 70 having a fracture 72 is schematically shown in section. The bone includes an inner medullary cavity 74 having a relatively narrow convergent portion 76 and a larger diameter divergent portion 78. Typically, the nail 50 is selected to have a maximum retracted diameter D3 which corresponds to the diameter of the convergent portion 76. This permits the expandable end of the nail 50, when it is in a retracted position, to be inserted through the convergent portion 76 of the medullary cavity 74. After the nail has been inserted through the convergent portion 76 and into the divergent portion 78, the balls 56 can be expanded radially outwardly to an increased diameter D4 to engage the inner wall of the divergent portion of the medullary cavity 74. As was the case with the embodiment shown in FIGS. 1 through 5, the nail 50 provides at least two axially spaced apart support points (Pt. C and Pt. D) along the sleeve 50 at the increased diameter D4.

Although the above-discussed embodiments include an expandable portion located at only one end of the elongate sleeve, it will be appreciated that the other end of the sleeve could be readily modified to include a second expandable portion of similar design.

In accordance with the provisions of the patent statutes, the principal and mode of operation of the invention have been explained in what is considered to represent its best embodiments. It should, however, be understood that the invention may be practiced otherwise than as specifically illustrated and described without departing from its spirit or scope.

What is claimed is:

1. A fixation device for insertion into a medullary cavity of a bone comprising:

an elongate member defining a longitudinal axis and having one end adapted to be inserted within the medullary cavity of the bone, said one end having a predetermined maximum diameter to permit insertion of said one end within the bone cavity;

a plurality of circumferentially spaced, radially expandable elements carried by said one end of said member, said elements being radially movable from a first, retracted position wherein said elements define a first diameter to a second, expanded position wherein said elements define a second diameter greater than said predetermined maximum diameter and said first diameter, each of said elements including a radially outermost portion adapted to engage the inner wall of the bone cavity, said radially outermost portions of said elements in said second position providing at least two spaced apart support points at said second diameter and located along an axis generally parallel to the longitudinal axis of said elongate member, said radially outermost portions of said elements providing said support points being maintained at a generally equal spacing from the longitudinal axis of said elongate members as said elements are moved from said first position to said second position;

means carried by said elongate member for moving said elements from said first position to said second position; and actuator means located at the other end of said elongate member and coupled to operate said moving means for controlling the radial position of said elements.

2. The fixation device according to claim 1 wherein said elongate member is a sleeve provided with a plurality of circumferentially spaced openings for receiving said radially expandable elements.

3. The fixation device according to claim 2 including means for maintaining said elements within said openings.

4. The fixation device according to claim 2 wherein said radially expandable elements are each provided with an axially extending outer surface for engagement with the inner wall of the bone cavity, said outer surface providing said axially spaced apart support points when said elements are in said second position.

5. The fixation device according to claim 4 wherein said moving means includes cam means engagable with said elements for positioning said outer surface of said elements at a selected position defining a diameter between said first and second diameters.

6. The fixation device according to claim 5 wherein said actuator means is an elongate shaft extending axially through said sleeve and mounted for selective rotational movement within said sleeve, said cam means being responsive to the rotational movement of said shaft for controlling the radial position of said elements.

* * * * *